United States Patent
Harris et al.

(10) Patent No.: US 10,918,729 B2
(45) Date of Patent: *Feb. 16, 2021

(54) OSTEOSTIMULATING ELASTOMERIC BONE FILLING COMPOSITIONS

(71) Applicant: THE SECANT GROUP, LLC, Telford, PA (US)

(72) Inventors: Jeremy J. Harris, Doylestown, PA (US); Charles Brendan Nicholson, Coopersburg, PA (US); Peter D. Gabriele, Frisco, TX (US); Jared Ely, Quakertown, PA (US); Brian Ginn, Chalfont, PA (US)

(73) Assignee: THE SECANT GROUP, LLC, Telford, PA (US)

(*) Notice: Subject to any disclaimer, the term of this patent is extended or adjusted under 35 U.S.C. 154(b) by 90 days.

This patent is subject to a terminal disclaimer.

(21) Appl. No.: 16/263,064

(22) Filed: Jan. 31, 2019

(65) Prior Publication Data

US 2019/0231890 A1    Aug. 1, 2019

Related U.S. Application Data

(60) Provisional application No. 62/624,579, filed on Jan. 31, 2018, provisional application No. 62/720,296, filed on Aug. 21, 2018.

(51) Int. Cl.
| | |
|---|---|
| A61L 27/18 | (2006.01) |
| A61K 47/59 | (2017.01) |
| A61K 47/34 | (2017.01) |
| A61L 24/06 | (2006.01) |
| C08K 3/013 | (2018.01) |
| C08G 63/12 | (2006.01) |
| C08J 3/12 | (2006.01) |
| A61P 19/00 | (2006.01) |
| C08L 67/00 | (2006.01) |
| A61L 27/48 | (2006.01) |
| A61L 27/56 | (2006.01) |

(52) U.S. Cl.
CPC ............ *A61K 47/593* (2017.08); *A61K 47/34* (2013.01); *A61L 24/06* (2013.01); *A61L 27/18* (2013.01); *A61L 27/48* (2013.01); *A61L 27/56* (2013.01); *A61P 19/00* (2018.01); *C08G 63/12* (2013.01); *C08J 3/12* (2013.01); *C08K 3/013* (2018.01); *C08L 67/00* (2013.01); *A61L 2400/08* (2013.01); *A61L 2430/02* (2013.01); *C08J 2367/02* (2013.01)

(58) Field of Classification Search
CPC ..................................................... A61L 27/18
See application file for complete search history.

(56) References Cited

U.S. PATENT DOCUMENTS

| | | | | |
|---|---|---|---|---|
| 5,217,712 A | * | 6/1993 | Pogany | ............... A61K 9/204 424/78.01 |
| 8,043,699 B2 | | 10/2011 | Rosing et al. | |
| 9,359,472 B2 | | 6/2016 | Nicholson et al. | |
| 10,525,140 B2 | * | 1/2020 | Wroblesky | ........... A61K 47/593 |
| 2010/0228358 A1 | * | 9/2010 | Leonard | ................ A61L 24/001 623/23.62 |
| 2011/0142790 A1 | * | 6/2011 | Chen | ..................... A61L 31/128 424/78.37 |
| 2012/0143347 A1 | | 6/2012 | Wang et al. | |
| 2017/0246316 A1 | | 8/2017 | Wroblesky et al. | |
| 2018/0280912 A1 | | 10/2018 | Lu et al. | |

FOREIGN PATENT DOCUMENTS

| | | |
|---|---|---|
| WO | 2017147457 A2 | 8/2017 |
| WO | 2018035475 A1 | 2/2018 |
| WO | 2018183856 A1 | 4/2018 |

OTHER PUBLICATIONS

S. H. Zaky, et al. "Poly(glycerol sebacate) elastomer supports bone regeneration by its mechanical properties being closer to osteoid tissue rather than to mature bone", Acta Biomaterialia, vol. 54, Jan. 19, 2017, pp. 95-106.

* cited by examiner

*Primary Examiner* — Michael F Pepitone
(74) *Attorney, Agent, or Firm* — McNees Wallace & Nurick LLC

(57) ABSTRACT

A bone filling composition includes a bone filler. The bone filler includes microparticles of at least one elastomeric material. The at least one elastomeric material includes a poly(glycerol sebacate)-based thermoset. The poly(glycerol sebacate)-based thermoset may be porous thermoset poly (glycerol sebacate) flour, thermoset poly(glycerol sebacate) microspheres, or a combination thereof. In some embodiments, the bone filling composition is a bone filling composite that further includes a carrier material including a poly(glycerol sebacate) resin. A method of forming a bone filling composite includes selecting a bone filler and mixing the bone filler with a carrier material to form the bone filling composite. A method of treating a bony defect includes molding a bone filling composite and placing the bone filling composite in the bony defect. The bone filling composite includes a bone filler mixed with a carrier material.

18 Claims, 3 Drawing Sheets

OSTEOSTIMULATING ELASTOMERIC BONE FILLING COMPOSITIONS

CROSS-REFERENCE TO RELATED APPLICATIONS

This application claims priority to and the benefit of U.S. Provisional Application No. 62/624,579 filed Jan. 31, 2018 and U.S. Provisional Application No. 62/720,296 filed Aug. 21, 2018, which are hereby incorporated by reference in their entirety.

FIELD OF THE INVENTION

The present application is generally directed to bone filling compositions. More specifically, the present application is directed to osteostimulating elastomeric bone filling compositions.

BACKGROUND OF THE INVENTION

The current state-of-the-art in bone filler devices is to use hydroxyapatite (HA; $Ca_{10}(PO_4)_6(OH)_2$) or other salts of calcium and phosphate as an osteoconductive material. The idea behind the use of the calcium salts is that they represent the mineral composition of hard bone in composition and physical properties. However, bone is composed of both hard osseous (cortical) tissue and softer osseous (cancellous) tissue, and during the healing process, bone first goes through a soft elastomeric (osteoid) phase prior to mineralization.

These changes in physical properties during the healing process provide mechano-biologic cues to the local cellular environment, promoting the expression of the appropriate cell types required at that phase of the healing process. The presence of such hard mineral biomaterials causes the expression of cell types for late-stage healing, thereby skipping the earlier osteoid period of healing. Current approaches to bone healing, using hard, brittle salts of calcium and phosphate to stimulate bone growth through simulation of the mechanical properties of mature cortical bone, disregard the tissue properties during the early phases of bone regeneration.

Commercial fillers are used in long bone defects and dental applications. These fillers contain a salt and may additionally include a carrier material, which may be a synthetic material or a biologic material, such as, for example, collagen. In some cases, plastic materials are included in the commercial filler. These plastic materials, however, do not transmit stress but instead shield adjacent materials from stress. The carrier only acts as a binding matrix to keep the calcium salt within the bone defect. It does not provide any therapeutic effect. If the filler contains only a salt, the filler is typically mixed with blood and placed within the defect.

The problems associated with conventional putty formulations include, but are not limited to, their inclusion of animal-based carrier materials, their inability to be molded to fit the defect geometry, their inability to remain in the defect site, their resistance to irrigation, their lack of antimicrobial properties, and the need for a two-step process of mixing salt with blood to achieve an appropriate consistency.

What is needed is an elastomeric bone filling composition that promotes the expression of the appropriate cell types during the early phases of bone regeneration.

BRIEF DESCRIPTION OF THE INVENTION

In an embodiment, a bone filling composition includes a bone filler. The bone filler includes microparticles of at least one elastomeric material and a filler dopant in the elastomeric material. The at least one elastomeric material includes a poly(glycerol sebacate)-based thermoset.

In another embodiment, a method of forming a bone filling composite includes selecting a bone filler. The method also includes mixing the bone filler with a carrier material to form the bone filling composite. The bone filler includes microparticles of at least one elastomeric material. The at least one elastomeric material includes a poly(glycerol sebacate)-based thermoset.

In yet another embodiment, a method of treating a bony defect includes molding a bone filling composite and placing the bone filling composite in the bony defect. The bone filling composite includes a bone filler mixed with a carrier material. The bone filler includes microparticles of at least one elastomeric material. The carrier material includes a poly(glycerol sebacate) resin.

Various features and advantages of the present invention will be apparent from the following more detailed description, taken in conjunction with the accompanying drawings which illustrate, by way of example, the principles of the invention.

BRIEF DESCRIPTION OF THE DRAWINGS

Wherever possible, the same reference numbers will be used throughout the drawings to represent the same parts.

DETAILED DESCRIPTION OF EXEMPLARY EMBODIMENTS

The use of a soft, elastomeric material promotes the natural bone healing cascade by first initiating the osteoid phase of bone healing. The elastomeric material transmits stress, which promotes the bone healing process.

In exemplary embodiments, bone growth is stimulated through the use of a bone filler through mechanisms that better reproduce the mechano-biologic response of the early phases of bone healing. The bone filler includes microparticles of at least one elastomeric material. The microparticles may include porous, elastomeric bone filling material and/or elastomeric microspheres.

In exemplary embodiments, the bone filler is part of a bone filling composition. In some embodiments, the bone filling composition is a bone filling composite. The bone filling composite includes a bone filler, an optional carrier material, and one or more optional carrier dopants. The bone filling composite is conformable and moldable, has a strong interaction/adhesion with tissue, and/or is ready-to-use out of the box.

In exemplary embodiments, the elastomeric material includes a poly(glycerol sebacate) (PGS)-based thermoset based on a PGS-based resin. In some embodiments, the PGS-based resin is a PGS resin. In exemplary embodiments, the PGS resin may be formed in a water-mediated reaction, such as described in U.S. Pat. No. 9,359,472, which is hereby incorporated by reference in its entirety, in the presence or in the absence of a doping mineral. The PGS resin may also be mixed with a porogen prior to curing and thermosetting. The PGS resin and porogen may be mixed at a weight-to-weight (w/w) ratio in the range of 1:1 to 1:3, alternatively 2:3 to 2:5, alternatively about 1:2, or any value, range, or sub-range therebetween. The porogen may then be removed by dissolving in an appropriate solvent to form microparticles of a porous thermoset PGS flour or porous thermoset PGS microspheres.

In exemplary embodiments, the microparticles of the bone filler include a porous thermoset PGS-based flour. In some embodiments, the porous thermoset PGS-based flour is a porous thermoset PGS flour. After forming the PGS resin and optionally mixing the PGS resin with a doping mineral and/or a porogen, the PGS resin may be cured and then ground to form the porous thermoset PGS flour. The porous thermoset PGS flour has an irregular surface contour and geometry. The curing and grinding to form the flour may be as described in U.S. Patent Application Publication No. 2017/0246316, which is hereby incorporated by reference in its entirety.

Figure 1:
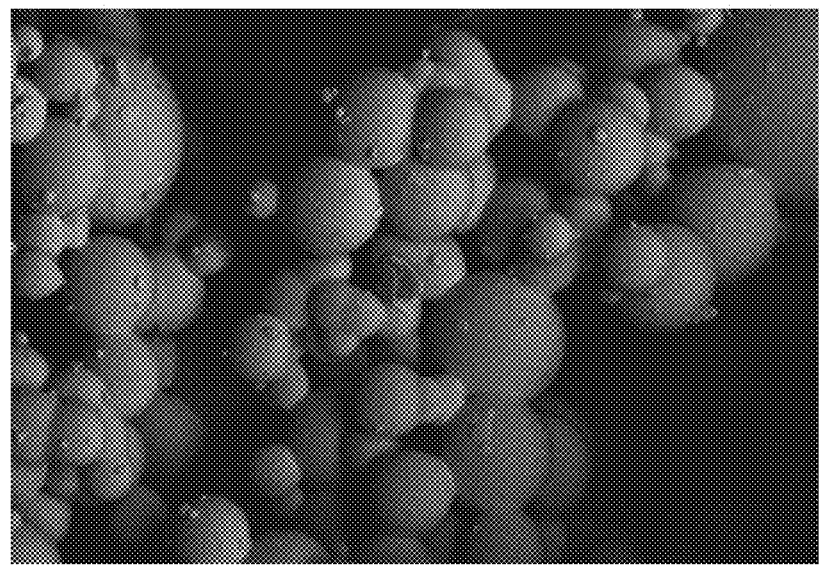
FIG. 1 is an image of thermoset PGS microspheres in an embodiment of the present disclosure.

In other exemplary embodiments, the microparticles of the bone filler include thermoset PGS-based microspheres. The thermoset PGS-based microspheres may be porous or non-porous. In some embodiments, the thermoset PGS-based microspheres are thermoset PGS microspheres. FIG. 1 is an image of thermoset PGS microspheres without pores. After forming the PGS resin and optionally mixing the PGS resin with a doping mineral and/or a porogen, the PGS resin may be cured to form the thermoset PGS microspheres. The PGS microspheres have a spherical geometry and a smooth surface contour. In exemplary embodiments, the thermoset PGS microspheres are formed without a mold by a method described in U.S. Patent Application Publication No. 2018/0280912, which is hereby incorporated by reference in its entirety.

In other exemplary embodiments, the microparticles of the bone filler include a mixture of porous thermoset PGS flour particles and thermoset PGS microspheres. The PGS flour particles have a highly irregular geometry in contrast to the highly regular geometry of the PGS microspheres. In exemplary embodiments, the relative amounts of PGS flour particles and PGS microspheres in the bone filler may be selected to provide a bone filling composition having a specific morphology for a specific application of the bone filling composition.

In other embodiments, the filler material includes another PGS-based thermoset material, such as, for example poly(glycerol sebacate urethane) (PGSU), poly(glycerol sebacate acrylate) (PGSA), or a PGS adduct with pendant groups, such as, for example, lysine (PGS-lysine) or salicylic acid (PGS-salicylic acid).

In exemplary embodiments, the porous thermoset PGS-based flour is formed from a PGS-based resin, a porogen, and an optional filler dopant. In exemplary embodiments, the thermoset PGS-based microspheres are formed from a PGS-based resin, a porogen, and an optional filler dopant.

Appropriate porogens may include an inorganic salt, bioglass, a sugar, or polymeric beads. Appropriate porogen inorganic salts may include, but are not limited to, sodium chloride (NaCl), potassium chloride (KCl), monocalcium phosphate ($Ca(H_2PO_4)_2$), dicalcium phosphate ($CaHPO_4$), tricalcium phosphate (TCP; $Ca_3(PO_4)_2$), monopotassium phosphate ($KH_2PO_4$), dipotassium phosphate ($K_2HPO_4$), tripotassium phosphate ($K_3PO_4$), or combinations thereof.

Suitable filler dopant materials may include, but are not limited to, a mineral, magnesium oxide (MgO), calcium oxide (CaO), dispersed hydroxyapatite, TCP, silicon dioxide ($SiO_2$), titanium dioxide ($TiO_2$), bioglass, magnesium chloride ($MgCl_2$), monomagnesium phosphate ($Mg(H_2PO_4)_2$), dimagnesium phosphate ($MgHPO_4$), magnesium phosphate tribasic ($Mg_3(PO_4)_2$), magnesium sulfate ($MgSO_4$), calcium chloride ($CaCl_2$)), monocalcium phosphate, dicalcium phosphate, tricalcium phosphate, calcium sulfate ($CaSO_4$), or combinations thereof.

In exemplary embodiments, the porous thermoset PGS flour is formed from a PGS resin having a weight average molecular weight in the range of 10 kilodaltons (kDa) to 20 kDa mixed with a porogen and cured for 24 to 96 hours, depending on the porogen concentration and the desired properties of the resultant flour. The cured mixture is then ground, and the ground mixture is exposed to a solvent that dissolves and removes the porogen while leaving the porous thermoset PGS flour. While any appropriate solvent may be used, the solvent is typically water or an aqueous solution. The resulting porous thermoset PGS flour may be used as bone filler.

As the resulting pore size is directly related to the particle size of the porogen, the size of the porogen may be selected based on the desired pore size, which may be based on the expected size of the flour particles. An appropriate size ratio of the average flour particle size to the average porogen particle size may be in the range of about 4:1 to about 10:1, alternatively in the range of about 5:1 to about 8:1, or any value, range, or sub-range therebetween. In some embodiments, the average particle size of the porogen is in the range of about 25 micrometers (μm) or less, alternatively about 25 μm to about 200 μm, alternatively about 25 μm to about 50 μm, alternatively about 50 μm to about 100 μm, or any value, range, or sub-range therebetween. The thermoset is then ground into a rough to fine flour with an average particle size of about 100 μm or less, alternatively 100 μm to 800 μm, alternatively 100 μm to 200 μm, alternatively 200 μm to 500 μm, or any value, range, or sub-range therebetween.

The thermoset PGS may be ground by any appropriate grinding process, including, but not limited to, cryomilling, disc milling, hammer milling, or ball milling, to form the PGS flour.

The molecular weight and/or the glycerol:sebacate stoichiometry of the PGS may be selected to provide a thermoset PGS flour with certain desired or predetermined properties. Alternatively or additionally, the PGS may be modified by the inclusion of MgO, bioglass, and/or acid.

In some embodiments, the composition of the PGS microspheres includes a PGS resin having a weight average molecular weight in the range of from about 5,000 to about 50,000 Da. In some such embodiments, the resin has a weight average molecular weight in the range of from about 10,000 to about 25,000 Da.

Different methods of microparticle forming technology, which may include, but are not limited to, emulsions, phase-separation, spray drying/congealing, spinning disk atomization, wax coating and hot melt, and freeze drying, may be utilized to form PGS microparticles or core-shell PGS microparticles prior to curing in a continuous matrix phase.

Depending on the materials and conditions, particles having a range of physical and chemical properties may be obtained. In some embodiments, the particles are microspheres having an average size in the range of 1 μm to 1 mm. In some embodiments, the microspheres have a particle size in the range of 50 μm to 300 μm, alternatively in the range of 100 μm to 500 μm, or any value, range, or sub-range therebetween.

Exemplary embodiments can provide for microspheres of PGS or other biodegradable polymers to be created and cured into an elastomer in one continuous step, allowing for the formation of microspheres that retain their spherical shape during thermal curing at elevated temperatures and/or microwave curing.

In some embodiments, concepts of microparticle formation and thermal curing of PGS are utilized and combined into a single step to form crosslinked PGS microspheres. In an exemplary embodiment, the process of making PGS microspheres occurs in a single vessel.

In some embodiments, neat PGS microspheres are manufactured by providing a liquid that is phase-incompatible with PGS. The phase-incompatible liquid may be any liquid or viscous medium that is phase-incompatible with the PGS. In some embodiments, the phase-incompatible liquid is non-reactive with the PGS, such as, for example, a mineral oil or a mixture of higher alkanes and/or cycloalkanes.

In some embodiments, methods take advantage of specific gravity and buoyancy in a vertical column. A phase-incompatible liquid of higher specific gravity than PGS fills a vertical column. A hypodermic needle inserted into the liquid at the bottom of the column permits introduction of the PGS resin from a reservoir. The vertical column and reservoir may be heated to allow flow. The vertical column may be surrounded with an appropriate radiation source, such as, for example, infrared (IR) or microwave, that is configured to deliver energy through the vertical column, the phase-incompatible liquid, and the PGS resin, to cure the PGS resin to a thermoset PGS microsphere.

The porous thermoset PGS flour and/or the thermoset PGS microspheres may be dusted or impregnated with salts of calcium and phosphate to provide additional osteoconductive cues while maintaining the elastomeric properties of the flour. Dusting may include tumbling or otherwise mixing the flour and/or microspheres in the salt to coat the flour and/or microsphere particles with the powder. Impregnation may include compressing the dusted or otherwise coated flour and/or microspheres to embed the powder in the particles.

The bone filler may contain demineralized bone matrix (DBM), bone chips, or other autologous materials that have been shown to be osteoinductive.

The bone filler may contain bone morphogenic proteins (BMPs) or other biologics that have been shown to enhance bone regeneration.

The PGS flour and/or PGS microspheres may be mixed with blood, serum, or another biologic medium prior to implantation. Alternatively, the PGS flour and/or PGS microspheres may be added directly to a bony void.

In exemplary embodiments, a bone filler formulated as described above is combined with a carrier material including a PGS resin to provide a bone filling composite as an out-of-the-box, moldable putty to be used to fill bony defects. PGS resin is a non-animal-based, non-inflammatory, resorbable binder for the bone filler. The PGS resin degrades faster than the PGS flour and/or PGS microspheres due to a lower crosslinking density of the PGS resin. As the resin degrades, any pores present in the flour and/or microspheres emerge and provide guidance cues for osteoblast infiltration. The elastomeric properties of the flour and/or microspheres simulate the mechanical forces of early bone growth, thereby promoting early collagen deposition.

Appropriate carrier materials may include, but are not limited to, PGS resin; a polypeptide, such as, for example, collagen; a polysaccharide, such as, for example, alginate; or a glycosaminoglycan, such as, for example, hyaluronic acid; a hydrogel; or combinations thereof. In some embodiments, the carrier material has antimicrobial properties. In some embodiments, the carrier material is a PGS resin. In some embodiments, the PGS resin carrier material is functionalized with other fatty acids or glycerol esters having antimicrobial properties, such as, for example, monolaurate.

The porous thermoset PGS flour and/or thermoset PGS microspheres may be mixed with a PGS resin composition to form a bone filling composite. The PGS resin composition includes a hot PGS resin and may include one or more carrier dopants. Carrier dopants may include, but are not limited to, glycerol, bioglass, one or more salts, or combinations thereof. Suitable carrier dopant materials may include, but are not limited to, a mineral, magnesium oxide, calcium oxide, dispersed hydroxyapatite, TCP, silicon dioxide, titanium dioxide, bioglass, magnesium chloride, monomagnesium phosphate, dimagnesium phosphate, magnesium phosphate tribasic, magnesium sulfate, calcium chloride, monocalcium phosphate, dicalcium phosphate, tricalcium phosphate, calcium sulfate, silver ions, a silver salt, or combinations thereof.

The elastomeric material and carrier dopant may be at a w/w ratio in the range of 1:1 to 1:3, alternatively 2:3 to 2:5, alternatively 2:3 to 1:2, alternatively 1:2 to 2:5, alternatively about 1:2, or any value, range, or sub-range therebetween. The elastomeric material and glycerol may be at a w/w ratio in the range of 10:1 to 2:1, alternatively 8:1 to 3:1, alternatively 5:1 to 3:1, alternatively 5:1 to 4:1, alternatively 4:1 to 3:1, alternatively about 5:1, alternatively about 4:1, alternatively about 3:1, or any value, range, or sub-range therebetween. The elastomeric material and hot PGS resin may be at a w/w ratio in the range of 2:1 to 1:2, alternatively 3:2 to 2:3, alternatively about 1:1, or any value, range, or sub-range therebetween. The hot PGS resin is preferably at a temperature of at least 90° C., such as, for example, 90° C. to 120° C. The carrier dopant may, for example, be a salt of calcium and phosphate, such as, for example, hydroxyapatite or TCP. In some embodiments, the porosity of the microparticles is selected based on trabecular bone properties. In some embodiments, the porosity of the porous thermoset PGS flour is in the range of 50% to 90%.

The PGS resin of the filler or the carrier may be synthesized to contain MgO, hydroxyapatite, TCP, bioglass, or another inorganic salt to mimic native bone. These inorganic additives may be part of the bone filler or resin carrier, where incorporation into the resin results in an early release to potentially accelerate healing.

Resin and/or flour particles and/or microsphere particles may be synthesized from monomers containing reactive moieties, such as, for example, acrylates, methacrylates, isocyanates, and/or sulfur, which allow the filler or carrier to cure in situ via heat, ultraviolet (UV) radiation, or another energy source.

In exemplary embodiments, the bone filling composite is molded to a shape of a bony defect and placed in the bony defect. The molding may occur before, during, and/or after placing the composite in the bony defect.

In exemplary embodiments, porous elastomeric particles placed in a bony defect provide the mechanobiologic cues of early-stage bone healing. The elastomeric particles stimulate bone growth, whereas conventional treatments use materials that are diametrically opposite to the elastomeric particles in physical properties.

A bone filling composite may be formulated into a sheet to act as a bone wrap. Such sheets may be used to augment bone plates or metal framing structures to encourage bone growth and incorporation of the metal structures.

Many current calcium and phosphate-containing particulates are fabricated using biologic scaffolds, such as, for example, algae, to form intricate 3D porous structures. PGS resin may also be used to fill similar templates to create novel 3D structures post-cure and post-template removal. Microfluidics may be used to fill micron-scale molds.

In some embodiments, compositions of the present disclosure are used in three-dimensional (3D) printing ink to form 3D articles for implantation.

MgO-doping provides an additional way to modify the physical properties of PGS thermosets, as the inclusion of MgO acts to increase the modulus, tensile strength, and elongation, as shown in the Examples. Without wishing to be bound by theory, the mechanism for this action may be due to direct coupling of the PGS polymer to the hydroxylated MgOH particles, increased hydrogen bonding, or through ionomer formation between the $Mg^{2+}$ and carboxylic acid groups present in the PGS.

In one application, the bone filling composition may aid in healing and recovery from femoral head deformity following ischemic necrosis, a fairly common deformation of children's hip joints. In cases of vascular disruption to the femoral head, the disruption of the blood supply to the femoral head may lead to bone, marrow, and cartilage necrosis and cessation of endochondral ossification in the femoral head. This weakens the femoral head such that it is no longer able to maintain its shape under the normal mechanical loadings on the femoral head. The resulting trabecular compression and deformation of the femur head leads to a hip joint displacement. Conventional recovery may include bedrest for up to a year to minimize the mechanical load while the femoral head heals.

Figure 2:
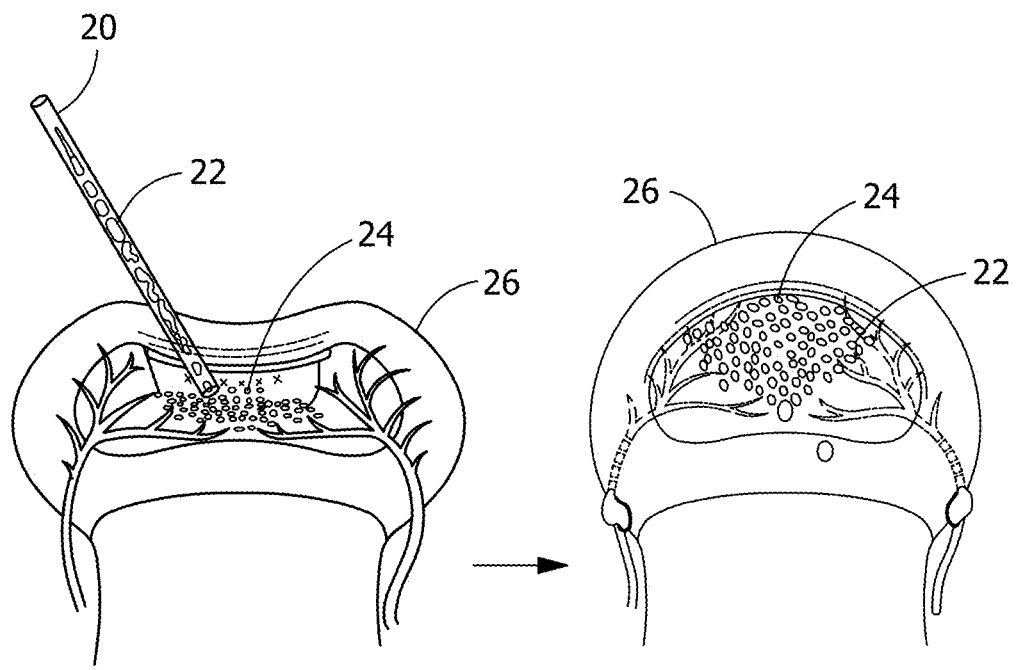
FIG. 2 shows a method of treatment using a bone filling composition of the present disclosure.

Referring to FIG. 2, after trabecular compression and deformation of the femur head, a cannula 20 is used to inject a bone filling composition including microparticles 22 into the necrotic trabecular space 24 of the femur head 26. The bone filling composition can be used to fill, inflate, maintain, and reform the void space. The microparticles 22 aid in re-scaffolding and remodeling the necrotic void, and the elastomeric nature of the microparticles 22 allows for rebuilding and re-ossification of the resorbed areas and restoration of the shape of the femur head 26. The microparticles 22 may be doped (e.g. with MgO) or undoped and may include porous thermoset PGS flour, thermoset PGS microspheres, or a combination of flour and microspheres. In some embodiments, microspheres are preferred, as the form of the microparticles 22 may be more amenable to injection through a cannula 20 into the necrotic trabecular space 24.

EXAMPLES

The invention is further described in the context of the following examples which are presented by way of illustration, not of limitation.

Example 1

A porous thermoset PGS flour was produced by first adding about 15 grams (g) of hot (≥90° C.) PGS resin to about 30 g of sieved, crystalline NaCl salt having an average particle size about 106 μm or less. The materials were mixed by a mixer (FlackTek, Inc., Landrum, S.C.) at 2000 revolutions per minute (rpm) for about 2 minutes. The resultant paste was placed into a round aluminum dish and smoothed to a film about 2 millimeters (mm) thick. The film was thermoset at a temperature of about 120° C. and a pressure of about 10 Torr for about 24 hours. The resultant solid film was removed from the aluminum dish in crumbled pieces and placed into a jar and then mixed by the FlackTek mixer at 2000 rpm for about 1 minute to break/grind the flour to smaller particle sizes.

About 50 mL of deionized water ($diH_2O$) was added to the jar and the jar was sonicated for about 5 minutes to dissolve away the NaCl salt. The solvent was decanted, and the dissolve step was repeated three times. The resultant flour was then transferred to a Büchner funnel with filter paper in place. The PGS flour was placed in the Buchner funnel and rinsed by vacuum filtration with 1000 mL of $diH_2O$. The resultant flour was dried in a vacuum desiccator at a pressure of about 10 Torr for about 18 hours. The PGS flour particles were imaged for size and porosity by scanning electron microscopy (SEM).

Example 2

A PGS bone filling composite was produced by adding about 2.5 g of the porous thermoset PGS flour from Example 1 to about 4.4 g of TCP particles having a particle size in the range of about 50-150 μm and about 0.6 g of glycerol. The materials were mixed by a FlackTek mixer at about 2000 rpm for about 30 seconds, followed by a dwell time of about 20 minutes. To this mixture, about 2.5 g of hot (≥90° C.) PGS resin was added as a carrier and mixed at about 2000 rpm for about 1 minute. The resultant bone filling composite was soft and moldable. The bone filling composite was characterized by manual manipulation and by SEM/energy dispersive X-ray spectroscopy (EDS) for organic/mineral homogeneity.

Example 3

An MgO-doped PGS resin was formed in a water-mediated reaction based on a method described in U.S. Pat. No. 9,359,472, which is hereby incorporated by reference in its entirety, where the MgO particles were introduced before the 24-hour distillation step. The MgO was provided in an amount of about a 1:200 weight ratio with respect to the PGS resin. Glycerol was added to a reaction vessel with water under stirring. After dissolution of the glycerol, sebacic acid was added to the reaction vessel. The amounts of glycerol and sebacic acid were selected to provide about a 3:2 molar ratio of free hydroxyl groups to free carboxyl groups. The reaction vessel was then fitted with a condenser to reflux water during the melt and stir steps of the polymerization, with the condenser temperature being set to 2.5° C. The reaction vessel was then heated to a temperature of 160° C. under stirring for approximately 70 minutes.

After the sebacic acid melted, the temperature was set to 150° C. and the mixture was stirred under reflux for 90 minutes.

The condenser was then removed, the MgO particles were added, and the reaction vessel was fitted with a distillation condenser to remove water from the reaction vessel. A nitrogen purge was applied to the reaction vessel and the temperature was set to 120° C. During the distillation, the contents of the reaction vessel were stirred at 120° C. for 24 hours.

Next, a vacuum line was connected to the distillation condenser and the sub-atmospheric pressure was applied to the contents of the reaction vessel. The pressure was reduced slowly and stepwise over about 120 minutes to approximately 20 Torr.

Once the pressure in the reaction vessel reached about 20 Torr, the vacuum pump was set to 10 Torr. Following the application of vacuum at about 10 Torr, the reaction vessel was left to react for 26 hours at 130° C. under stirring, with the sub-atmospheric pressure set to 10 Torr.

Example 4

In a parallel synthesis method to that of Example 3, an MgO-doped PGS resin was formed, where the MgO particles were introduced after the 24-hour distillation step rather than before the 24-hour distillation step as described in Example 3.

Example 5

A porous MgO-doped (about 0.5% w/w) PGS flour was prepared as in Example 1, except that unsieved NaCl salt was used in place of sieved NaCl salt, the MgO-doped PGS resin of Example 3 was used in place of neat PGS resin, and about a 1.5:1 w/w ratio of NaCl salt to MgO-doped PGS resin was used. The porous MgO-doped PGS flour was characterized by SEM/EDS for organic/mineral homogeneity, with the results being similar to those of Example 1.

Example 6

A porous MgO-doped PGS bone filling composite was produced by adding about 5.9 g of porous MgO-doped PGS flour from Example 3, to about 1.0 g of TCP particles having a particle size in the range of about 50-150 μm and about 0.6 g of glycerol. The materials were mixed in a FlackTek mixer at about 2000 rpm for about 30 seconds, followed by a dwell time of about 2 hours. To this mixture, about 2.5 g of hot (≥90° C.) MgO-doped PGS resin of Example 3 was added as a carrier and mixed at about 2000 rpm for about 1 minute. The resultant bone filling composite was soft and moldable. The porous MgO-doped PGS bone filling composite was characterized by SEM/EDS for organic/mineral homogeneity, with the results being similar to those of Example 2.

Example 7

Post-synthesis, the MgO-doped PGS resins of Example 3 and Example 4 were evaluated using differential scanning calorimetry (DSC) and were analyzed rheologically to assess the resins' thermal and rheological properties, respectively. The MgO-doped PGS resins of Example 3 and Example 4 were analyzed to evaluate the effect of hydroxylating the MgO and incorporating it into PGS.

A portion of each resin was loaded into an aluminum pan, targeting a film thickness of about 2 mm, and thermoset at about 120° C. for about 73.5 hours. As a control, three pans of stock PGS resin, produced by a similar synthesis method but not doped with MgO, were also thermoset with the same specifications alongside the MgO-doped PGS resin to provide control data for all thermoset properties. The resins and their respective thermosets were tested under DSC and tensile analyses to assess their thermal and mechanical properties. Tensile testing was performed according to ASTM D6381. Samples were also cut from each piece of thermoset material and crosslink density measurements were taken according to a method outlined in U.S. Pat. No. 8,043,699, which is hereby incorporated by reference in its entirety.

Figure 3:
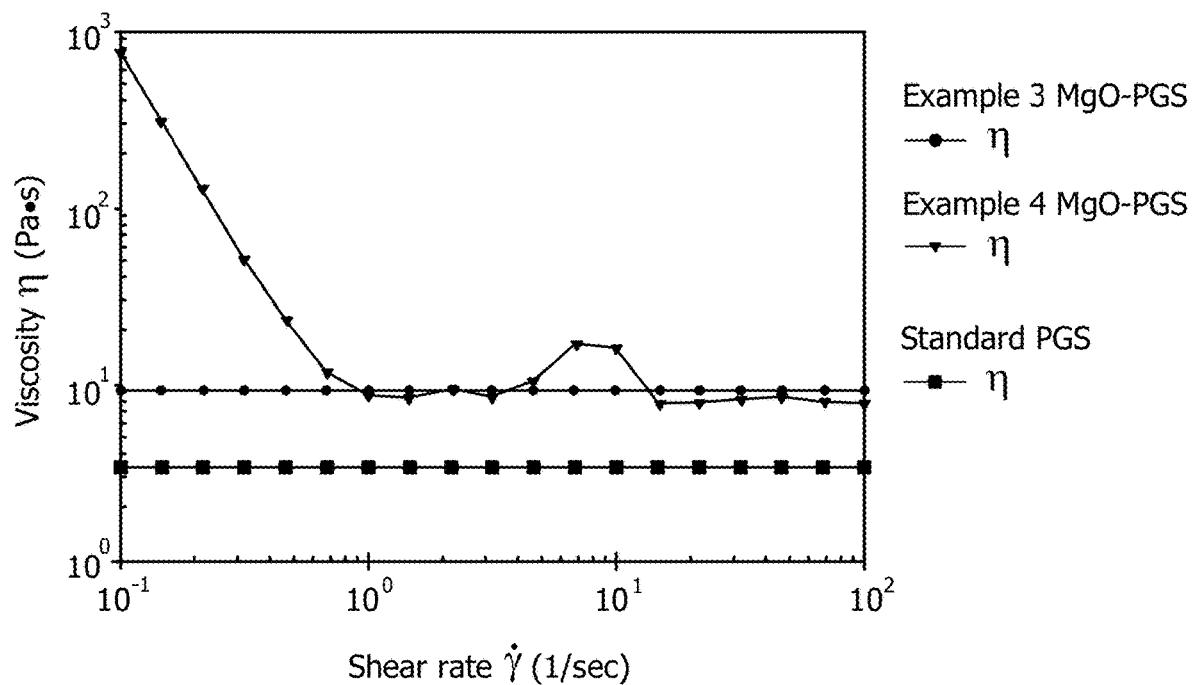
FIG. 3 shows the zero-shear viscosity profiles of MgO-doped PGS resins in embodiments of the present disclosure.

As observed in the reaction vessels, the MgO-doped PGS resin of Example 3 was slightly cloudy with no dispersed particulate, while the MgO-doped PGS resin of Example 4 had visible suspended particulate matter. FIG. 3 shows the control resin zero-shear viscosity profile, the Example 3 resin zero-shear viscosity profile, and the Example 4 resin zero-shear viscosity profile. These viscosity measurements, taken during rheological analysis, indicate that both MgO-doped PGS resins had substantially higher viscosities compared to typical PGS (about 9 Pa·s as compared to about 3 Pa·s, respectively), although the particulate in the resin from Example 4 caused the zero-shear viscosity profile to appear erratic.

Figure 4:
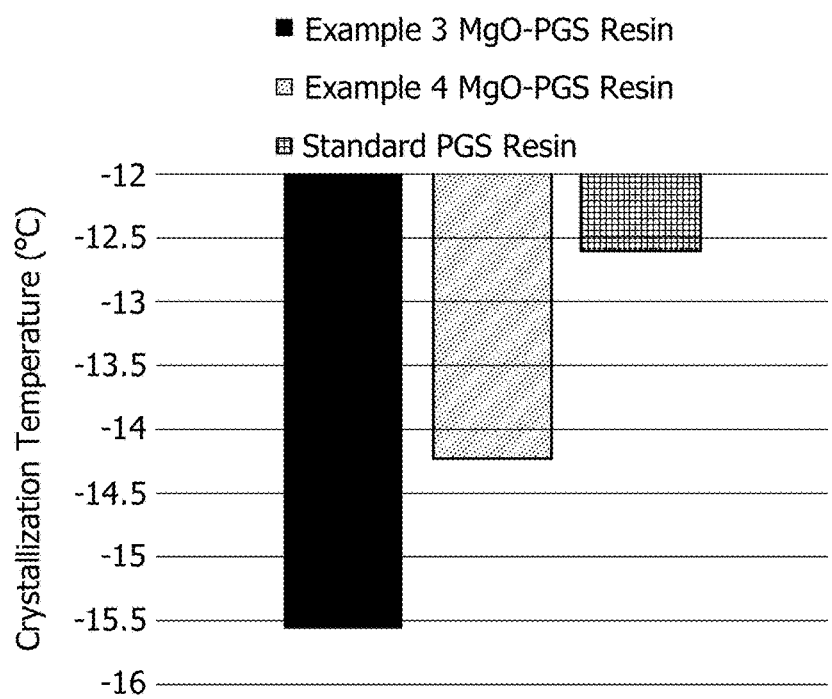
FIG. 4 shows the resin crystallization temperatures for PGS and for MgO-doped PGS resins in embodiments of the present disclosure.

DSC measurements of both the resinous and thermoset forms of the Example 3 MgO-doped PGS resin and thermoset, the Example 4 MgO-doped PGS resin and thermoset, and the control PGS resin and thermoset indicated that the MgO-doped PGS samples exhibited lower crystallization temperatures as compared to the PGS control samples. FIG. 4 shows the Example 3 resinous form crystallization temperature, the Example 4 resinous form crystallization temperature, and the undoped PGS control resinous form crystallization temperature. The depressed crystallization temperatures of the MgO-doped PGS samples, relative to the PGS control samples, may indicate a more reacted and/or crosslinked polymer, as that is the trend with undoped PGS. Other chemical interactions between the MgO and the PGS may also or alternatively influence the crystallization behavior of the material.

Figure 5:
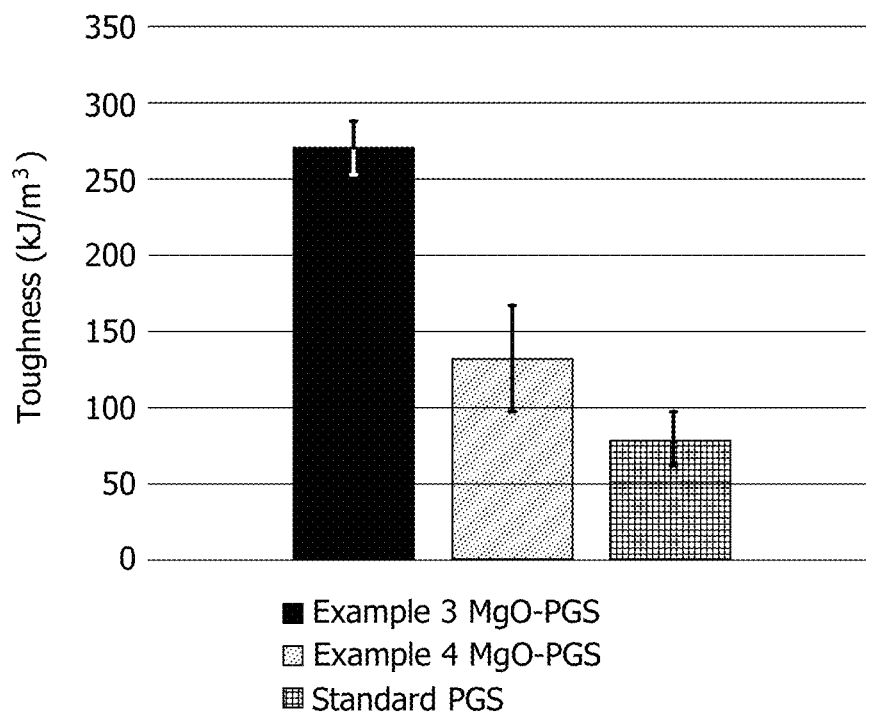
FIG. 5 shows the toughness values measured by tensile testing for control PGS and MgO-doped PGS of the present disclosure.

FIG. 5 shows the toughness values for the undoped PGS control thermosets, the Example 3 MgO-doped PGS thermosets, and the Example 4 MgO-doped PGS thermosets subjected to tensile testing. Overall, the MgO-doping yielded a tougher thermoset material as compared to the control PGS. The MgO-doped PGS thermoset of Example 3 had a higher toughness than that of the MgO-doped PGS thermoset of Example 4. Without wishing to be bound by theory, this can be explained in one of two ways: first, the process of Example 3 allowed the MgO material a greater chance to react with the PGS, as the MgO was added earlier in the polymerization process, more hydroxylation of the MgO from water contained in the reactor vessel, and/or better homogeneity in the final product as compared to the Example 4 process. Second, the larger/non-uniform size of the embedded MgO particulate in the Example 4 thermoset may have caused stress concentrations in the material during tensile testing, thereby instigating smaller strains to failure.

As noted above, preparation of the composition of Example 4 only differed from preparation of the composition of Example 3 in that the MgO was introduced before the distillation step for the composition of Example 3 but the MgO was introduced after the distillation step for the composition of Example 4. FIG. 3 through FIG. 5, however, illustrate that this preparation change had a measurable effect on the resulting physical properties of the compositions. Introducing the MgO before the distillation step provided a much flatter zero-shear viscosity profile, slightly lower crystallization temperatures for the resin and the thermoset, and a significantly greater toughness of the resulting composition relative to introducing the MgO after the distillation step.

Figure 6:
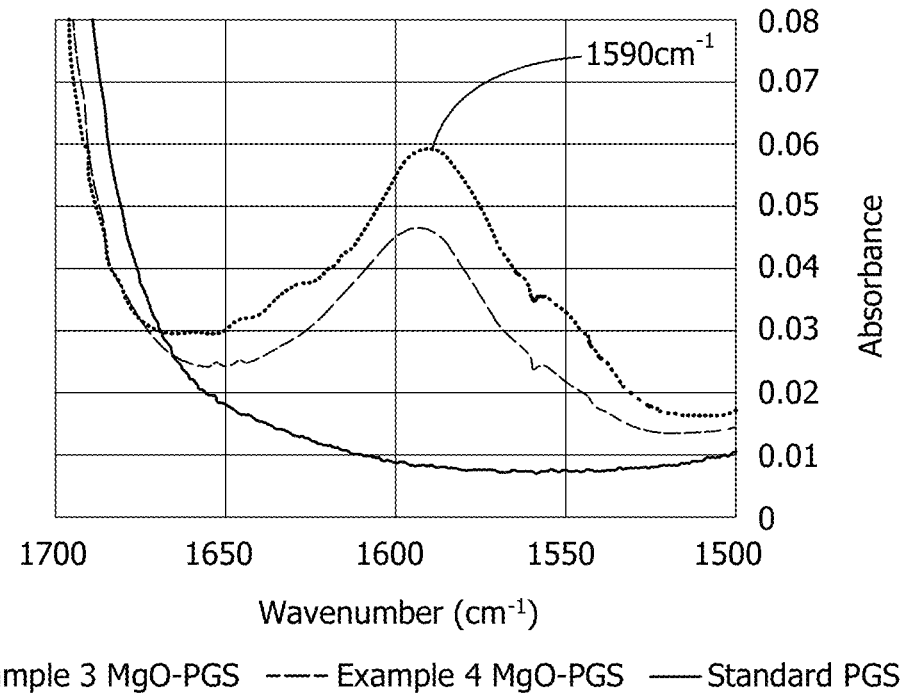
FIG. 6 shows FTIR spectra of thermoset PGS and thermoset MgO-doped PGS of the present disclosure.

Finally, as shown in FIG. 6, Fourier-transform infrared (FTIR) analysis of the thermoset samples revealed an absorbance peak at about 1590 cm$^{-1}$ for both the Example 3 MgO-doped PGS thermoset FTIR spectrum and the Example 4 MgO-doped thermoset FTIR spectrum that is not present in the control PGS thermoset FTIR spectrum. Without wishing to be bound by theory, this absorption peak may be due to either coordination of the Mg$^{2+}$ species by the negatively-charged carboxylic acids of PGS or by esterification of the PGS to the hydroxylated surface of the Mg(OH)$_2$ particles.

While the invention has been described with reference to one or more exemplary embodiments, it will be understood by those skilled in the art that various changes may be made, and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. In addition, all numerical values identified in the detailed description shall be interpreted as though the precise and approximate values are both expressly identified.

What is claimed is:

1. A bone filling composite comprising:
   a bone filler comprising:
      microparticles of at least one elastomeric material comprising a poly(glycerol sebacate)-based thermoset; and
      a filler dopant in the at least one elastomeric material; and
   a carrier material mixed with the bone filler, the carrier material comprising:
      a poly(glycerol sebacate) resin; and
      at least one carrier dopant comprising glycerol and tricalcium phosphate.

2. The bone filling composite of claim 1, wherein the poly(glycerol sebacate)-based thermoset is a porous thermoset poly(glycerol sebacate) flour.

3. The bone filling composite of claim 1, wherein the poly(glycerol sebacate)-based thermoset is thermoset poly(glycerol sebacate) microspheres.

4. The bone filling composite of claim 1, wherein the poly(glycerol sebacate)-based thermoset is a combination of a porous thermoset poly(glycerol sebacate) flour and thermoset poly(glycerol sebacate) microspheres.

5. The bone filling composite of claim 1, wherein the filler dopant comprises magnesium oxide.

6. The bone filling composite of claim 1, wherein the filler dopant is selected from the group consisting of magnesium oxide, calcium oxide, dispersed hydroxyapatite, tricalcium phosphate, silicon dioxide, titanium dioxide, bioglass, magnesium chloride, monomagnesium phosphate, dimagnesium phosphate, magnesium phosphate tribasic, magnesium sulfate, calcium chloride, monocalcium phosphate, dicalcium phosphate, calcium sulfate, and combinations thereof.

7. The bone filling composite of claim 1, wherein the at least one carrier dopant further comprises a compound selected from the group consisting of magnesium oxide, calcium oxide, dispersed hydroxyapatite, silicon dioxide, titanium dioxide, bioglass, magnesium chloride, monomagnesium phosphate, dimagnesium phosphate, magnesium phosphate tribasic, magnesium sulfate, calcium chloride, monocalcium phosphate, dicalcium phosphate, calcium sulfate, silver ions, a silver salt, and combinations thereof.

8. A method of forming a bone filling composite, the method comprising:
   selecting a bone filler comprising microparticles of at least one elastomeric material comprising a poly(glycerol sebacate)-based thermoset; and
   mixing the bone filler with a carrier material comprising a first poly(glycerol sebacate) resin to form the bone filling composite;
   wherein the first poly(glycerol sebacate) resin is at a temperature of at least 90° C.

9. The method of claim 8, wherein the poly(glycerol sebacate)-based thermoset is selected from the group consisting of porous thermoset poly(glycerol sebacate) flour, thermoset poly(glycerol sebacate) microspheres, and a combination thereof.

10. The method of claim 8, wherein the temperature of the first poly(glycerol sebacate) resin is in the range of 90° C. to 120° C.

11. The method of claim 8 further comprising mixing a filler second poly(glycerol sebacate) resin with a porogen to form a mixture, curing the mixture to thermoset the second poly(glycerol sebacate) resin, grinding the mixture, and removing the porogen by dissolution in a solvent to form the microparticles as a porous thermoset poly(glycerol sebacate) flour.

12. The method of claim 11 further comprising doping the second poly(glycerol sebacate) resin with a filler dopant.

13. The method of claim 11, wherein the porogen is selected from the group consisting of sodium chloride, potassium chloride, monocalcium phosphate, dicalcium phosphate, tricalcium phosphate, monopotassium phosphate, dipotassium phosphate, tripotassium phosphate, and combinations thereof.

14. The method of claim 8 further comprising doping the first poly(glycerol sebacate) resin with a carrier dopant.

15. A method of treating a bony defect, the method comprising:
   molding a bone filling composite and placing the bone filling composite in the bony defect;
   wherein the bone filling composite comprises a bone filler mixed with a carrier material comprising a poly(glycerol sebacate) resin; and
   wherein the bone filler comprises microparticles of at least one elastomeric material.

16. The method of claim 15, wherein the at least one elastomeric material comprises a poly(glycerol sebacate)-based thermoset selected from the group consisting of a porous thermoset poly(glycerol sebacate) flour, thermoset poly(glycerol sebacate) microspheres, and a combination thereof.

17. The method of claim 15, wherein the bone filler further comprises a filler dopant in the microparticles of at least one elastomeric material.

18. The method of claim 15, wherein the carrier material further comprises a carrier dopant mixed with the poly(glycerol sebacate) resin.

* * * * *